United States Patent
Helmer et al.

(10) Patent No.: US 11,260,183 B2
(45) Date of Patent: Mar. 1, 2022

(54) INJECTION NEEDLE ASSEMBLY

(71) Applicant: Sanofi-Aventis Deutschland GMBH, Frankfurt am Main (DE)

(72) Inventors: Michael Helmer, Frankfurt am Main (DE); Matthias Rau, Wiesbaden (DE); Winfried Huthmacher, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 254 days.

(21) Appl. No.: 16/317,479

(22) PCT Filed: Jul. 12, 2017

(86) PCT No.: PCT/EP2017/067507
§ 371 (c)(1),
(2) Date: Jan. 11, 2019

(87) PCT Pub. No.: WO2018/011253
PCT Pub. Date: Jan. 18, 2018

(65) Prior Publication Data
US 2019/0224424 A1    Jul. 25, 2019

(30) Foreign Application Priority Data
Jul. 14, 2016   (EP) .................................... 16179487

(51) Int. Cl.
*A61M 5/32*      (2006.01)
*A61M 5/24*      (2006.01)
(Continued)

(52) U.S. Cl.
CPC ........ *A61M 5/3245* (2013.01); *A61M 5/2466* (2013.01); *A61M 5/3213* (2013.01);
(Continued)

(58) Field of Classification Search
CPC .. A61M 5/3245; A61M 39/04; A61M 5/3213; A61M 2005/3254;
(Continued)

(56) References Cited

U.S. PATENT DOCUMENTS

| 5,069,669 A | 12/1991 | Kole |
| 2004/0014781 A1 | 1/2004 | Elger et al. |

(Continued)

FOREIGN PATENT DOCUMENTS

| CN | 102125711 | 7/2011 |
| CN | 103619381 | 3/2014 |

(Continued)

OTHER PUBLICATIONS

"Resilient" definion, https://www.merriam-webster.com/dictionary/resilient (Year: 2021).*

(Continued)

*Primary Examiner* — Theodore J Stigell
*Assistant Examiner* — Rachel T. Smith
(74) *Attorney, Agent, or Firm* — Fish & Richardson P.C.

(57) ABSTRACT

The present disclosure relates to an injection needle assembly for use in a medicament delivery device. The injection needle assembly comprises an injection needle holder, an injection needle fixed to said injection needle holder, the injection needle having a proximal end and a distal end, and a sealing assembly for sealing the distal end of the injection needle. The sealing assembly comprises a spacer element surrounding the distal end of the injection needle and a sealing membrane for sealing the distal end of the injection needle.

17 Claims, 6 Drawing Sheets

(51) Int. Cl.
  *A61M 39/04* (2006.01)
  *A61M 5/50* (2006.01)
  *A61M 39/02* (2006.01)
  *A61M 39/10* (2006.01)

(52) U.S. Cl.
  CPC .......... *A61M 5/3243* (2013.01); *A61M 39/04* (2013.01); *A61M 5/3202* (2013.01); *A61M 5/50* (2013.01); *A61M 5/5086* (2013.01); *A61M 2005/247* (2013.01); *A61M 2005/3254* (2013.01); *A61M 2039/0205* (2013.01); *A61M 2039/1072* (2013.01); *A61M 2205/0216* (2013.01); *A61M 2207/00* (2013.01)

(58) Field of Classification Search
  CPC .. A61M 2039/0205; A61M 2039/1072; A61M 2207/00; A61M 2005/247
  See application file for complete search history.

(56) References Cited

U.S. PATENT DOCUMENTS

| | | | |
|---|---|---|---|
| 2004/0210197 | A1* | 10/2004 | Conway .......... A61B 5/150259 604/198 |
| 2015/0005734 | A1 | 1/2015 | Inoue et al. |
| 2018/0185588 | A1* | 7/2018 | Limaye ............... A61M 5/3243 |
| 2019/0262533 | A1* | 8/2019 | Bengtsson ............. A61M 5/24 |

FOREIGN PATENT DOCUMENTS

| | | | |
|---|---|---|---|
| CN | 104010615 | 8/2014 | |
| CN | 104812426 | 7/2015 | |
| CN | 104884106 | 9/2015 | |
| EP | 2799056 | 11/2014 | |
| JP | 2000-3 54627 | 12/2000 | |
| JP | 2004-305720 | 11/2004 | |
| JP | 2012-500679 | 1/2012 | |
| JP | 2013-542021 | 11/2013 | |
| WO | WO 2001/091797 | 12/2001 | |
| WO | WO 2012/158135 | 11/2012 | |
| WO | WO-2012158135 A1 * | 11/2012 | .......... A61M 5/3272 |
| WO | WO 2014/076225 | 5/2014 | |
| WO | WO 2014/080020 | 5/2014 | |

OTHER PUBLICATIONS

International Preliminary Report on Patentability in Application No. PCT/EP2017/067507, dated Jan. 15, 2019, 9 pages.
International Search Report and Written Opinion in Application No. PCT/EP2017/067507, dated Nov. 17, 2017, 12 pages.

* cited by examiner

INJECTION NEEDLE ASSEMBLY

CROSS REFERENCE TO RELATED APPLICATIONS

The present application is the national stage entry of International Patent Application No. PCT/EP2017/067507, filed on Jul. 12, 2017, and claims priority to Application No. EP 16179487.0, filed on Jul. 14, 2016, the disclosures of which are incorporated herein by reference.

TECHNICAL FIELD

The present disclosure relates to an injection needle assembly for use in a medicament delivery device. The present invention also relates to a device for delivery of medicament to a patient, the device containing an injection needle assembly.

BACKGROUND

Medicament injection devices such as auto-injectors are a common type of medicament delivery devices designed to deliver a medicament by injection. This type of devices are designed to be easy to use and intended for self-administration by patients, or administration by persons having no formal medical training.

Some medicament injection devices operate with a cartridge-based injection system. This type of injection devices is typically provided with a separate cartridge pre-filled with medicament and a separate needle assembly sealed in a sterilised packaging. Before the injection, the patient has to place the cartridge in a cartridge holder located within the housing of the device, unseal the packaging containing the needle assembly, and position the needle assembly in the housing of the device. Therefore, the patient has to perform several steps before being able to carry out the injection, which can be time-consuming and uncomfortable, in particular for patients of impaired physical ability. Another problem is that, prior use in the device, the needle can be damaged, e.g. by being exposed to a relatively broad range of temperature during warehousing and/or transportation, and may also be subject to unintended bending during assembly process.

Medicament injection devices operating with a syringe-based injection system also exist. This type of injection devices typically comprises a syringe pre-filled with medicament having a needle already fixed to the body of the syringe. Before the injection, the patient places the syringe in the housing of the device. During the injection, the whole syringe is moved forward to penetrate the patient's skin. The syringes used with this latter type of devices are often stored during a relatively long time before being effectively used for injection. One problem is that, during this time of storage, the medicament remains in contact with the needle of the syringe and a clogging of the needle by the medicament may occur. This may delay the delivery of medicament during the injection and therefore increase the injection time.

At least in certain embodiments, the present disclosure sets out to overcome or ameliorate at least some of the problems mentioned above.

SUMMARY

Aspects of the present invention relate to a needle assembly for use in a medicament delivery device.

According to a further aspect of the present invention, there is provided an injection needle assembly for use in a medicament delivery device, comprising an injection needle holder, an injection needle fixed to said injection needle holder, the injection needle having a proximal end and a distal end, and a sealing assembly for sealing the distal end of the injection needle, wherein the sealing assembly comprises a spacer element surrounding the distal end of the injection needle and a sealing membrane for sealing the distal end of the injection needle.

The spacer element may be deformable. The spacer element may be made of a resilient material. The sealing assembly may be movable between a storage configuration in which the spacer element is in an extended state such that the spacer element entirely surrounds the distal end of the injection needle, and a use configuration in which the spacer element is in a retracted state such that the distal end of the injection needle extends beyond the spacer element. This may advantageously allow protection of the injection needle prior to use, but allow exposure of the injection needle upon application of sufficient force to deform the spacer element.

In one embodiment, the injection needle assembly is configured to couple to a medicament delivery device comprising a cartridge for medicament, and wherein the sealing membrane is configured to seal the distal end of the injection needle prior to the injection needle assembly being coupled to said medicament delivery device.

The spacer element may comprise a central passage through which the injection needle extends. The central passage may be configured such that the injection needle is not in contact with the spacer element. This may advantageously facilitate ease of insertion of the needle during assembly, and/or exposure of the needle in use.

The spacer element may be fixed to the injection needle holder. This may advantageously facilitate ease of manufacture/assembly of the injection needle assembly, and/or avoid movement of the spacer element in use.

In the storage configuration, the spacer element may be sealed within the sealing membrane. This may advantageously help maintain the needle sterile before use.

The distal end of the injection needle may be configured to pierce the sealing membrane when the sealing assembly moves from the storage configuration towards the use configuration. This may advantageously help ensure the needle remains sterile until the immediate moment before injection is to occur.

The injection needle assembly may comprise a deformable injection needle shield for shielding the proximal end of the injection needle. The injection needle shield may be deformable between a shielding position in which the injection needle shield is in an extended state such that the injection needle shield entirely surrounds the proximal end of the injection needle, and a retracted position in which the injection needle shield is in a retracted state such that the proximal end of the injection needle extends beyond the injection needle shield. This may advantageously enable ease of exposure of the proximal end of the needle prior to use, and/or avoid having to remove the needle shield prior to use.

The injection needle holder may comprise an engaging element configured to engage a corresponding engaging element of the medicament delivery device to connect the injection needle assembly to the medicament delivery device. This may advantageously facilitate ease of attachment of the injection needle holder to a medicament delivery device.

In one embodiment, the sealing membrane comprises a deformable cover.

A further aspect of the present invention provides a medicament delivery device assembly comprising an injection needle assembly as described above and a medicament delivery device comprising a cartridge for medicament. The medicament delivery device assembly may be in the form of an injection device, for example, an auto-injector.

The injection needle assembly may be releasably connected to the medicament delivery device.

In one embodiment, the cartridge contains medicament.

In one embodiment, there is provided an injection needle assembly for coupling to a medicament delivery device comprising a cartridge for medicament, the injection needle assembly comprising: an injection needle holder; an injection needle fixed to said injection needle holder, the injection needle having a proximal end and a distal end; and a sealing assembly for sealing the distal end of the injection needle; wherein the sealing assembly comprises a spacer element surrounding the distal end of the injection needle and a sealing membrane for sealing the distal end of the injection needle prior to the injection needle assembly being coupled to said medicament delivery device.

A further aspect of the present invention provides a method of assembling a medicament delivery device assembly, the method comprising: providing a medicament delivery device comprising a cartridge; providing an injection needle assembly comprising an injection needle holder, an injection needle fixed to said injection needle holder and having a proximal end and a distal end, and a sealing assembly having a spacer element surrounding the distal end of the injection needle and a sealing membrane that seals the distal end of the injection needle prior to the injection needle assembly being coupled to the medicament delivery device; and, coupling the injection needle assembly to the medicament delivery device.

BRIEF DESCRIPTION OF THE FIGURES

Exemplary embodiments of the present invention are described with reference to the accompanying drawings, in which.

DETAILED DESCRIPTION

Embodiments of the present invention provide an injection needle assembly for use in a medicament delivery device, the injection needle assembly having an injection needle, a sealing assembly comprising a spacer element surrounding a distal end of the injection needle and a sealing membrane for sealing the distal end of the injection needle. Providing such a sealing assembly allows the injection needle to remain sterile and protected during storage and/or transportation prior use in the medicament delivery device. The needle assembly in accordance with certain aspects of the present invention allows for a more comfortable and efficient use of the device. Indeed, in embodiments of the present invention, the user does not need to touch the needle during the steps of unsealing the distal end of the needle, inserting the needle into the medicament cartridge and actuating the injection of the medicament.

Figure 1A:
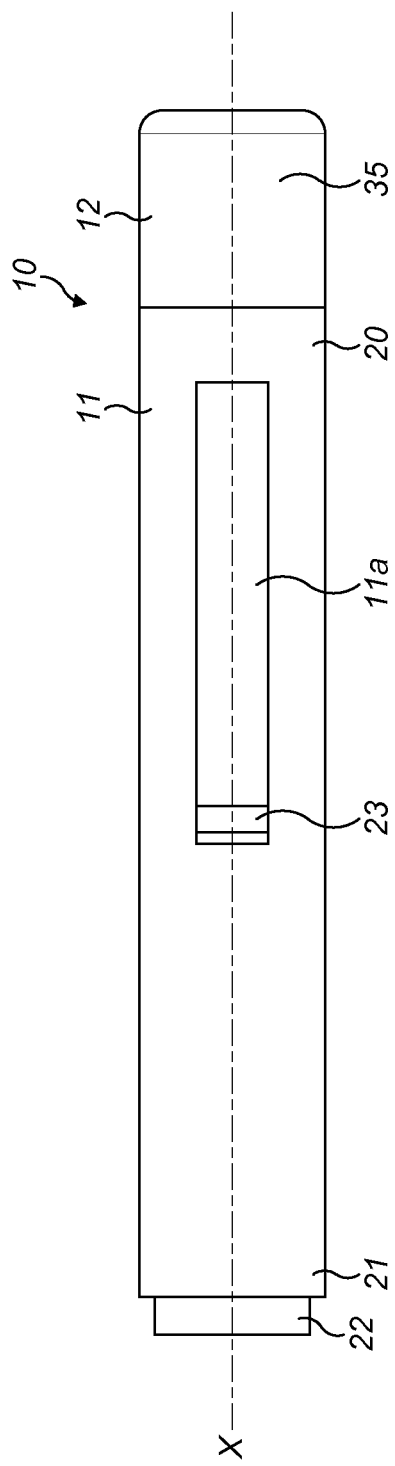
FIGS. 1A and 1B show schematic side views of a medicament delivery device assembly which may include embodiments of the injection needle assembly of the present invention.
Figure 1B:
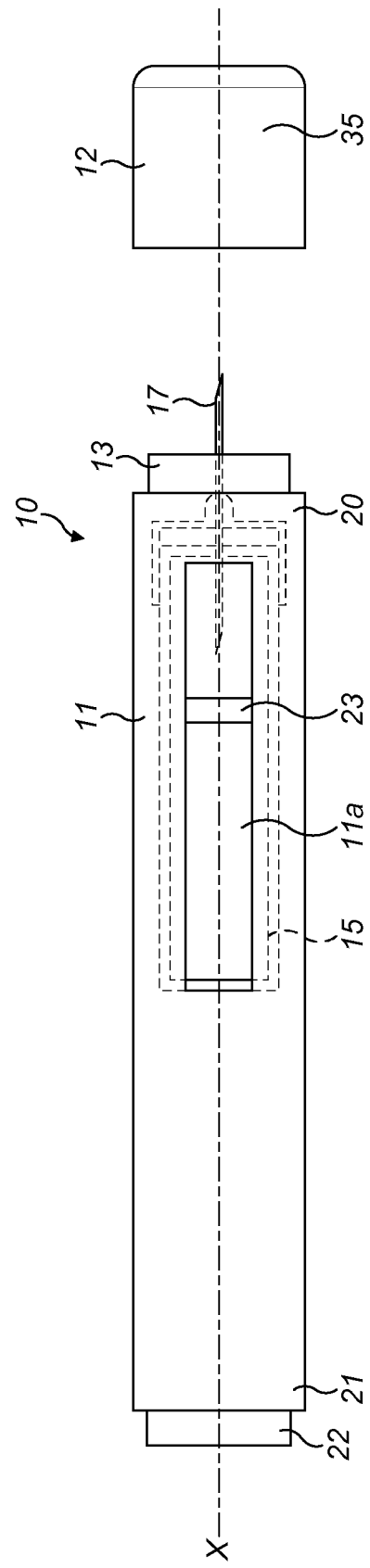

According to some embodiments of the present disclosure, an exemplary medicament delivery device assembly comprising a drug delivery device 10, herein simply referred to as "device 10", is shown in FIGS. 1A and 1B.

The terms "proximal" and "distal" herein respectively refer to as relatively closer to the patient and relatively further away from the patient.

The device 10, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml.

Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Device 10, as described above, is configured to inject a medicament, e.g. a liquid medicament, into a patient's body. Device 10 includes a body or housing 11 which typically contains a reservoir containing the medicament to be injected (e.g., a cartridge) and the components required to facilitate one or more steps of the delivery process. Device 10 can also include a cap assembly 12 that can be detachably mounted to the housing 11. Typically a user must remove the cap assembly 12 from the housing 11 before the device 10 can be operated.

Figure 2:
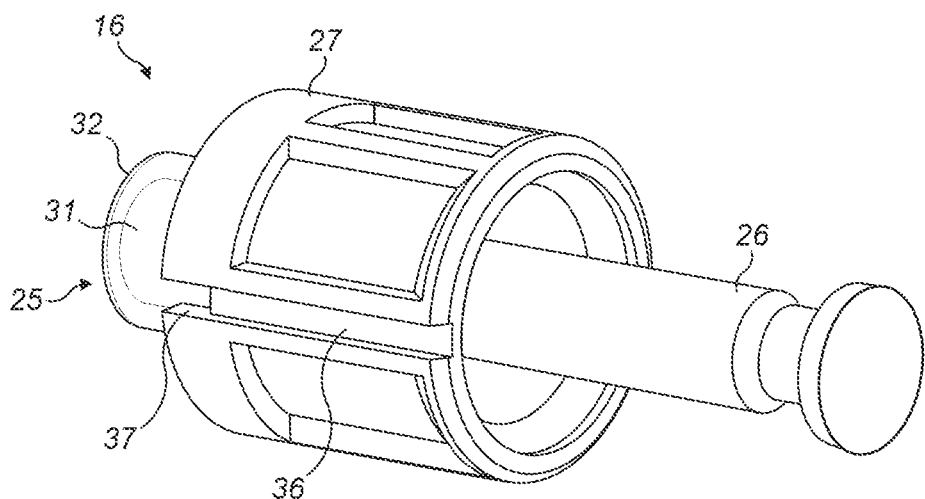
FIG. 2 shows a perspective view of an injection needle assembly according to a first embodiment of the present invention, the injection needle assembly being in a storage configuration.

The device 10 includes a cartridge 15 pre-filled with liquid medicament. The medicament delivery device assembly comprises the device 10 and a pen needle or needle assembly 16 (shown in FIG. 2) comprising an injection needle 17 for injecting medicament from the cartridge 15 to a patient's body. The injection needle 17 is in the form of a hollow needle 17 comprising a proximal end 18, a distal end 19, and an intermediate section 24 extending between the proximal end 18 and the distal end 19. The proximal end 18 is intended to be inserted in a patient's body. The distal end 19 is intended to be inserted in the cartridge 15. The housing 11 includes a window 11a, through which the contents of the cartridge 15 can be viewed. As shown in FIG. 2, the needle assembly 16 also comprises a sealing assembly 25 or sterile packaging 25 for sealing the distal end 19 of the injection needle 17, and an injection needle shield 26 for shielding the proximal end 18 of the injection needle 17.

As shown, the housing 11 is substantially cylindrical and has a substantially constant diameter along the longitudinal axis X. The housing 11 has a proximal region 20 and a distal region 21. The term "proximal" refers to a location that is relatively closer to a site of injection, and the term "distal" refers to a location that is relatively further away from the injection site.

The device 10 can also include a needle sleeve 13 coupled to housing 11 to permit movement of sleeve 13 relative to housing 11. The sleeve 13 is retractably mounted in the housing 11. For example, sleeve 13 can move in a longitudinal direction parallel to longitudinal axis X. Specifically, movement of the sleeve 13 in a distal direction can permit the needle 17 to extend from the proximal region 20 of the housing 11.

Insertion of the needle 17 can occur via several mechanisms. For example, the needle 17 may be fixedly located relative to housing 11 and initially be located within an extended needle sleeve 13. Distal movement of the sleeve 13 by placing a proximal end 18 of the sleeve 13 against a patient's body and moving the housing 11 in a proximal direction will uncover the proximal end 18 of the needle 17. Such relative movement allows the proximal end 18 of the needle 17 to extend into the patient's body. Such insertion is termed "manual" insertion as needle 17 is manually inserted via the patient's manual movement of the housing 11 relative to the sleeve 13.

Another form of insertion is "automated," whereby the needle 17 moves relative to housing 11. Such insertion can be triggered by movement of sleeve 13 or by another form of activation, such as, for example, a button 22. As shown in FIGS. 1A and 1B, button 22 is located at a distal end 19 of housing 11. However, in other embodiments, button 22 could be located on a side of housing 11.

Other manual or automated features can include drug injection or needle retraction, or both. Injection is the process by which a bung or piston 23 is moved from a distal location within a cartridge 15 to a more proximal location within the cartridge 15 in order to force a medicament from the cartridge 15 through the needle 17. In some embodiments, a drive spring (not shown) is under compression before the device 10 is activated. A distal end 19 of the drive spring can be fixed within distal region 21 of housing 11, and a proximal end 18 of the drive spring can be configured to apply a compressive force to a distal surface of piston 23. Following activation, at least part of the energy stored in the drive spring can be applied to the distal surface of piston 23. This compressive force can act on piston 23 to move it in a proximal direction. Such proximal movement acts to compress the liquid medicament within the cartridge 15, forcing it out of the needle 17.

Following injection, needle 17 can be retracted within sleeve 13 or housing 11. Retraction can occur when sleeve 13 moves proximally as a user removes device 10 from a patient's body. This can occur as needle 17 remains fixedly located relative to housing 11. Once a proximal end 18 of sleeve 13 has moved past a proximal end 18 of needle 17, and needle 17 is covered, sleeve 13 can be locked. Such locking can include locking any distal movement of sleeve 13 relative to housing 11.

Another form of needle retraction can occur if needle 17 is moved relative to housing 11. Such movement can occur if the cartridge 15 within housing 11 is moved in a distal direction relative to housing 11. This distal movement can be achieved by using a retraction spring (not shown), located in proximal region 20. A compressed retraction spring, when activated, can supply sufficient force to the cartridge 15 to move it in a distal direction. Following sufficient retraction, any relative movement between needle 17 and housing 11 can be locked with a locking mechanism. In addition, button 22 or other components of device 10 can be locked as required.

Figure 3A:
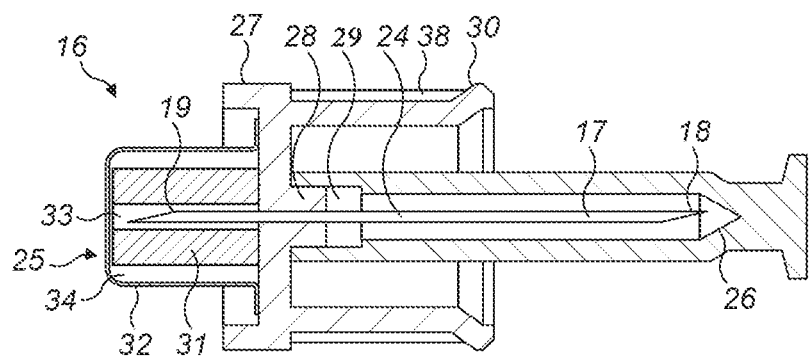
FIG. 3A shows a cross-sectional view of the injection needle assembly shown in FIG. 2, the injection needle assembly being in the storage configuration.
Figure 3B:
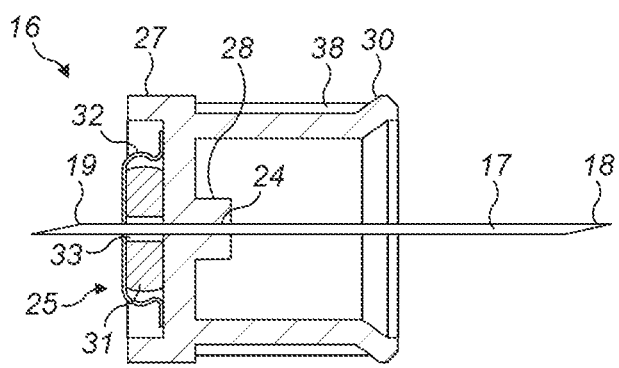
FIG. 3B shows a cross-sectional view of the injection needle assembly shown in FIG. 2, the injection needle assembly being in a use configuration.

A first embodiment 16 of the needle assembly is shown in FIGS. 2, 3A and 3B. The needle assembly 16 comprises an injection needle holder or holding body 27 to which the injection needle 17 is fixed. As visible in FIG. 2, the needle holder 27 has a substantially cylindrical outer shape. The needle holder 27 comprises a needle supporting portion 28 having a needle hub 29 to which the intermediate section 24 of the needle 17 is secured. The needle holder 27 comprises a flange 30 extending proximally from the needle supporting portion 28. The needle supporting portion 28 supports the needle 17 in a position substantially parallel to the longitudinal axis X when the needle assembly 16 is secured in the device 10. The needle supporting portion 28 supports the needle 17 such that the flange 30 surrounds the intermediate section 24 of the needle 17. The needle supporting portion 28 supports the needle 17 such that the proximal end 18 extends proximally beyond the flange 30 and such that the distal end 19 extends distally beyond the needle holder 27.

The sealing assembly 25 serves as a needle protection. The sealing assembly 25 is arranged to seal the distal end 19 of the injection needle 17 such that the distal end 19 remains sterile and protected prior use of the needle 17 in the device 10. The sealing assembly 25 comprises a deformable spacer element 31 surrounding the distal end 19 for protecting the distal end 19, and a sealing membrane 32 for sealing the distal end 19. The sealing assembly 25 is movable between a storage configuration, or assembled state, and a use configuration, or activated state. In the storage configuration, the spacer element 31 is in an extended state such that the spacer element 31 entirely surrounds the distal end 19. In the use configuration, the spacer element 31 is in a retracted state such that the distal end 19 extends distally beyond the spacer element 31.

The spacer element 31 is fixed to the injection needle holder 27 and extends longitudinally along the distal end 19. The spacer element 31 comprises a central passage 33 through which the distal end 19 extends. The central passage 33 is substantially tubular. The diameter of the central passage 33 is such that the needle 17 is not in contact with the spacer element 31. In other words, the central passage 33 is designed to prevent any contact between the spacer element 31 and the distal end 19. The central passage 33 thereby helps preventing particles from getting into the needle 17 and contaminating the drug. The spacer element 31 is designed in such a way that the spacer element 31 is prevented from getting in contact with the needle 17 and therefore with the drug, whether the spacer element 31 is in the storage configuration or in the use configuration. The spacer element 31 is made of a resilient material, for example made of foam. Alternatively, the spacer element 31 may comprise a spring.

The spacer element 31 protects the needle 17 in such a way that the needle 17 is able to withstand variable temperature ranges during transportation and/or warehousing prior use in the device 10. In addition, the spacer element 31 prevents the needle 17 from unintended bending during transportation and/or warehousing and/or assembly process. Moreover, providing the spacer element 31 to protect the needle 17 enables a lower clean or grey room class handling during manufacturing. Furthermore, providing the spacer element 31 allows the needle assembly 16 to be more resistant and less sensitive than needle assemblies known from the state of the art such as needle assemblies in which the needle 17 is only protected by a sealing foil.

The sealing membrane 32 is in the form of a deformable cover. The sealing membrane 32 is for example made of foil. The sealing membrane 32 is fixed to the needle holder 27 such that in the storage configuration, the sealing membrane 32 and the needle holder 27 form a sterile volume 34 within which the spacer element 31 and the distal end 19 of the needle 17 extend. The sealing membrane 32 is fixed to the needle holder 27 for example by gluing, welding or shrinking.

When the sealing assembly 25 is in the storage configuration, the spacer element 31 extends beyond the distal end 19 of the needle 17. Therefore, when the sealing assembly 25 is in the storage configuration, the spacer element 31 prevents the distal end 19 of the needle 17 from damaging or piercing the sealing membrane 32. The sealing membrane 32 is arranged relative to the distal end 19 of the needle 17 in such a way that the distal end 19 pierces the sealing membrane 32 when the sealing assembly 25 moves from the storage configuration towards the use configuration.

The cap assembly 12 comprises an outer cap 35, shown in FIGS. 1A and 1B, and the inner needle shield 26, shown in FIGS. 2, 3A and 3B. The inner needle shield 26 locates in the outer cap 35. The needle shield 26 encloses the proximal end 18 of the needle 17 to protect the proximal end 18 when the device 10 is not in use. The needle shield 26 seals the proximal end 18 against environmental conditions and prevents contamination of the proximal end 18. The needle shield 26 is substantially tubular. The needle shield 26 is made of a rigid material. The needle shield 26 is for example in the form of a plastic cap. The diameter of the needle shield 26 is such that an internal surface of the needle 17 cap tightly abuts the needle hub 29 to securely locate the needle shield 26 thereon.

The needle assembly 16 is configured to be releasably connected to the device 10. To this end, the injection needle holder 27 comprises a guiding element 36 configured to engage a corresponding guiding element (not shown) in the body of the device 10. As visible in FIGS. 2, 3A and 3B, the guiding element 36 is in the form of a guiding groove 36 extending along the external circumference of the needle holder 27. The guiding groove 36 is configured to engage a corresponding guiding projection (not shown) in the device 10 to guide the needle holder 27 in the device 10. As shown in FIG. 2, a locating recess 37 is provided on an external wall 38 of the needle holder 27 for engaging with a corresponding locating projection (not shown) in the device 10 to secure the needle assembly 16 to the device 10.

The operation of the injection needle assembly 16 in accordance with certain aspects of the present invention will now be described.

Initially, a cartridge 15 is inserted in the device 10 and the cap assembly 12 is mounted to the housing 11. The needle assembly 16 is provided as a separate component and is in the storage configuration, i.e. the spacer element 31 is in an extended state and surrounds entirely the distal end 19 of the needle 17, and both the spacer element 31 and the distal end 19 are sealed within the sealing membrane 32. The proximal end 18 of the needle 17 is enclosed in the needle shield 26 which abuts against the needle hub 29.

Then, the needle assembly 16 is placed in the housing 11 such that the groove on the needle holder 27 engages the projection in the housing 11. The inserted cartridge 15 is then pressed proximally towards the needle assembly 16. The spacer element 31 is compressed by the cartridge 15 and the sealing membrane 32 is deformed by the cartridge 15 towards the distal end 19 of the needle 17 such that the distal end 19 pierces the sealing membrane 32 and the cartridge 15. The device 10 is then ready to be used to perform an injection.

To perform an injection, the outer cap 35 is removed from the housing 11. As the outer cap 35 is removed, the outer cap 35 carries the needle shield 26 away from the needle holder 27 and thereby uncovers the proximal end 18 of the needle 17. The sleeve 13 is retracted into the housing 11 so that the proximal end 18 of the needle 17 projects outside the device 10. The medicament is then injected to the patient in a well-known manner. After the injection, the sleeve 13 extends again in the deployed position so that the sleeve 13 covers the proximal end 18 of the needle 17 for safe disposal of the device 10.

Figure 4A:
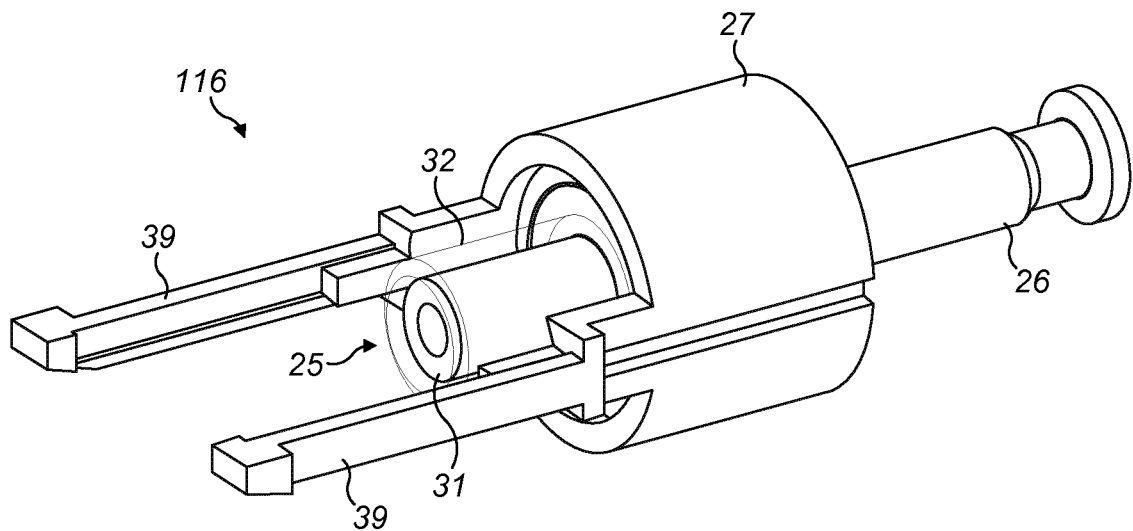
FIG. 4A shows a perspective view of an injection needle assembly according to a second embodiment of the present invention, the injection needle assembly being in a storage configuration.
Figure 4B:
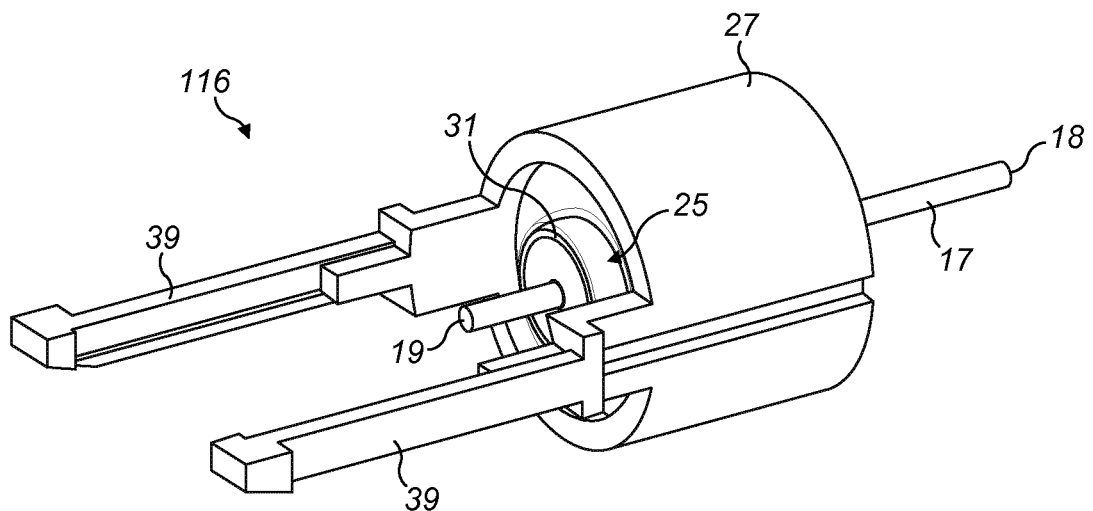
FIG. 4B shows a perspective view of the injection needle assembly shown in FIG. 4A, the injection needle assembly being in a use configuration.

An injection needle assembly 116 of a second embodiment of the invention is shown in FIGS. 4A and 4B and is similar to that of the first embodiment, and so like features retain the same reference numerals and a detailed description thereof will not be repeated.

A difference between the needle assembly 116 of the second embodiment and that of the first embodiment is that the needle assembly 116 of the second embodiment comprises engaging elements 39 configured to engage corresponding engaging elements (not shown) of the device 10. The engaging elements 39 are in the form a pair of hooks 39. The hooks 39 extend distally from the needle holder 27. The hooks 39 extend substantially parallel to each other.

The present invention is not intended to be limited to the particular types of connection between the needle assembly and the device shown in the drawings. It will be appreciated that any other geometries of the needle holder 27 configured to guide and secure the needle assembly inside the device are possible.

In the embodiments described above, the needle assemblies 16, 116 are described as being configured to be releasably connected to the device. However, the invention is not limited to such needle assemblies and the needle assembly according to certain aspects of the present invention can be pre-assembled in the device before use. The needle assembly according to the present invention can be, for example, permanently attached to the device and/or to the cartridge.

Figure 5A:
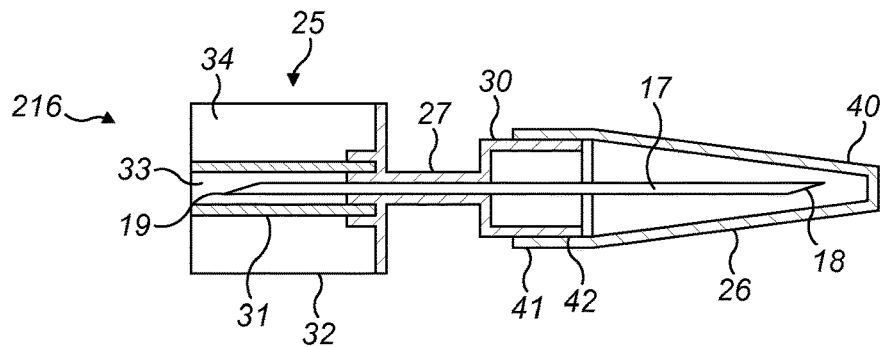
FIG. 5A shows a cross-sectional view of an injection needle assembly according to a third embodiment of the present invention, the injection needle assembly being in the storage configuration.
Figure 5B:
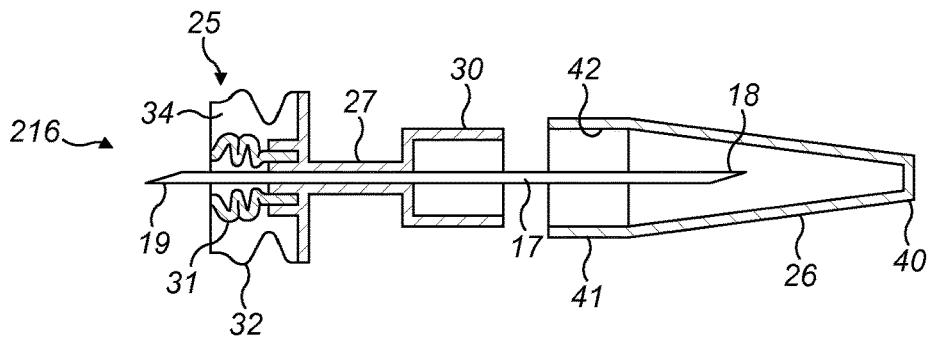
FIG. 5B shows a cross-sectional view of the injection needle assembly shown in FIG. 5A, the injection needle assembly being in a use configuration.

An injection needle assembly 216 of a third embodiment of the invention is shown in FIGS. 5A and 5B and is similar to that of the first embodiment, and so like features retain the same reference numerals and a detailed description thereof will not be repeated.

A difference between the needle assembly 216 of the third embodiment and that of the first embodiment is that in the needle assembly 216 of the third embodiment, the needle shield 26 is secured to the flange 30 of the needle holder 27. The needle shield 26 comprises a proximal portion 40 and a distal portion 41. The proximal portion 40 is generally cone-shaped and encloses the proximal end 18 of the needle 17. The distal portion 41 locates over the flange 30. The distal portion 41 has a generally cylindrical shape. The distal portion 41 is such that an internal surface 42 of the distal portion 41 tightly abuts the flange 30 of the needle holder 27 to securely locate the needle shield 26 thereon.

Figure 6A:
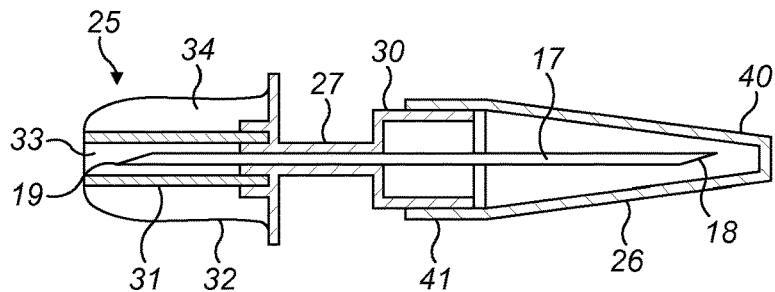
FIG. 6A shows a cross-sectional view of a first variant of the injection needle assembly shown in FIG. 5A, the injection needle assembly being in the storage configuration.
Figure 6B:
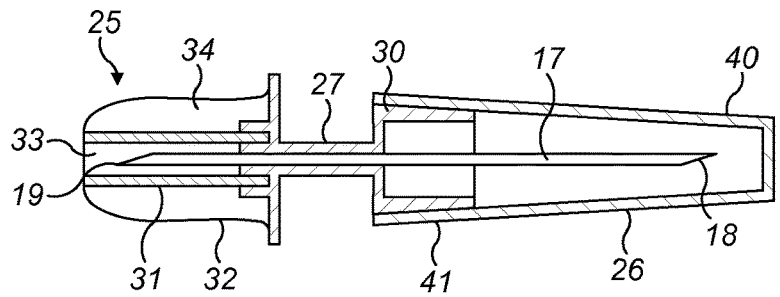
FIG. 6B shows a cross-sectional view of a second variant of the injection needle assembly shown in FIG. 5A, the injection needle assembly being in the storage configuration.
Figure 6C:
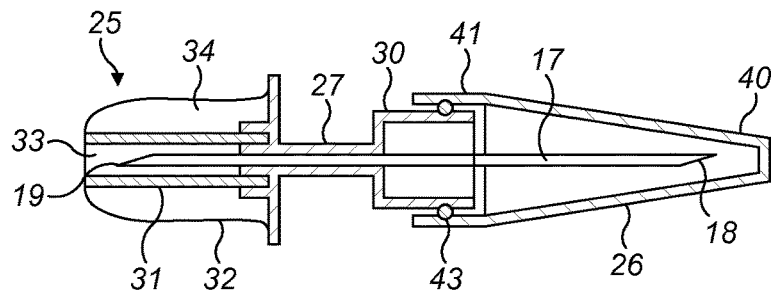
FIG. 6C shows a cross-sectional view of a third variant of the injection needle assembly shown in FIG. 5A, the injection needle assembly being in the storage configuration.
Figure 6D:
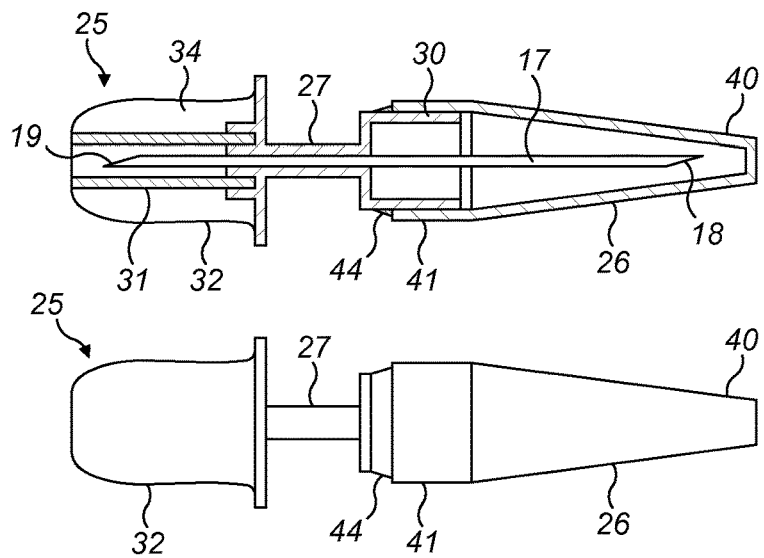
FIG. 6D shows cross-sectional and side views of a fourth variant of the injection needle assembly shown in FIG. 5A, the injection needle assembly being in the storage configuration.
Figure 6E:
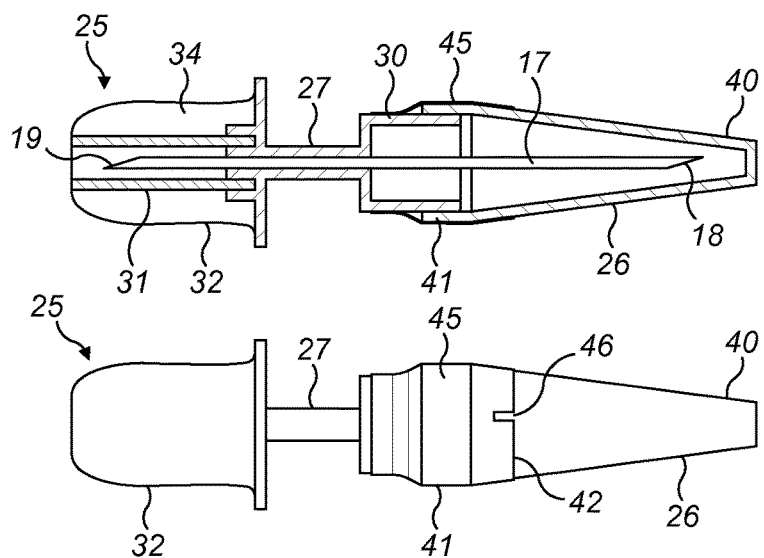
FIG. 6E shows cross-sectional and side views of a fifth variant of the injection needle assembly shown in FIG. 5A, the injection needle assembly being in the storage configuration.

In an alternative embodiment of the third embodiment, represented in FIG. 6B, the external surface of the flange 30 is conical and the distal portion 41 has a corresponding conical shape which tightly abuts the external surface. The distal portion 41 is for example made of an elastic material such as thermoplastic polymer or rubber. In a variant, a thread connection or a luer-lock connection may be provided to connect the distal portion 41 to the flange 30. In an alternative embodiment, represented in FIG. 6C, an additional sealing component 43 such as an O-ring 43 is provided between the flange 30 and the distal portion 41 of the needle shield 26 to seal the needle shield 26 on the needle holder 27. The O-ring 43 may be assembled on the needle holder 27 by a 2 k or two-shot injection molding process. The O-ring 43 is for example made of thermoplastic polymer or plastics. In a further alternative embodiment, represented in FIG. 6D, the distal portion 41 of the needle shield 26 abuts the flange 30 of the needle holder 27 to locate the needle shield 26 thereon, and is sealed to the flange 30 by means of a sealing compound 44, such as sealing varnish. In a still further alternative embodiment, shown in FIG. 6E, the distal portion 41 of the needle shield 26 abuts the flange 30 of the needle holder 27 to locate the needle shield 26 thereon, and is sealed to the flange 30 by means of a sealing film or coat 45, for example made from shrinkable tubing. A nick or small straight cut or pull linkage 46 extends a small distance from an end 47 of the coat 45 in a longitudinal direction of the coat 45. The nick 46 is provided on the coat 45 to help a user to easily remove the coat 45 from the needle assembly.

Figure 7A:
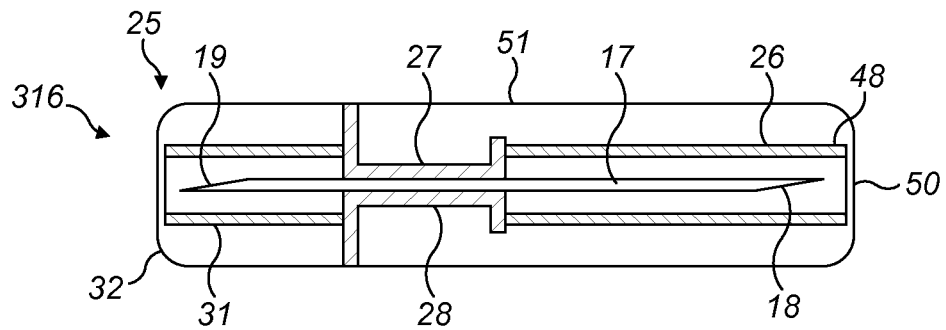
FIG. 7A shows a cross-sectional view of an injection needle assembly according to a fourth embodiment of the present invention, the injection needle assembly being in the storage configuration.
Figure 7B:
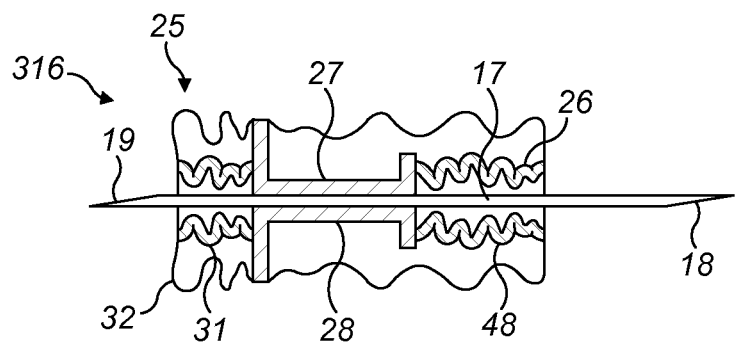
FIG. 7B shows a cross-sectional view of the injection needle assembly shown in FIG. 7A, the injection needle assembly being in a use configuration.

An injection needle assembly 316 of a fourth embodiment of the invention is shown in FIGS. 7A and 7B and is similar to that of the first embodiment, and so like features retain the same reference numerals and a detailed description thereof will not be repeated.

A difference between the needle assembly 316 of the fourth embodiment and that of the first embodiment is that both the spacer element 31 and the needle shield 26 are made of flexible tubes. The flexible shielding tube 48 forming the needle shield 26 is fixed to the needle supporting portion 28 at one end and sealed by a sealing film 50 at the opposite end. The shielding tube 48 is deformable between a shielding position and a retracted position. In the shielding position, the shielding tube 48 is in an extended state such that the shielding tube 48 entirely surrounds the proximal end 18 of the needle 17. In the retracted position, the shielding tube 48 is in a retracted state or compressed state such that the proximal end 18 of the needle 17 extends beyond the shielding tube 48. The shielding tube 48 is arranged relative to the needle 17 in such a way that the proximal end 18 pierces the sealing film 50 of the shielding tube 48 when the shielding tube 48 moves from the shielding position towards the retracted position. Another difference between the needle assembly 316 of the fourth embodiment and that of the first embodiment is that the sealing membrane 32 extends over the entire needle assembly 316. The sealing membrane 32 forms a protecting volume 51 in which the entire needle assembly 316 is enclosed when the needle assembly 316 is in the storage configuration. The sealing membrane 32 may be fixed to the needle holder 27, for example by gluing, welding or shrinking. The sealing membrane 32 is arranged relative to the distal end 19 of the needle 17 in such a way that the distal end 19 pierces the sealing membrane 32 when the sealing assembly 25 moves from the storage configuration towards the use configuration. Likewise, the sealing membrane 32 is arranged relative to the proximal end 18 of the needle 17 in such a way that the proximal end 18 pierces the sealing membrane 32 when the shielding tube 48 moves from the shielding position towards the retracted position.

Figure 8:
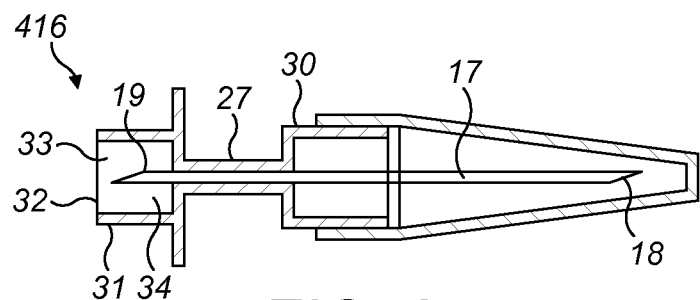
FIG. 8 shows a cross-sectional view of an injection needle assembly according to a fifth embodiment of the present invention, the injection needle assembly being in the storage configuration.

An injection needle assembly 416 of a fifth embodiment of the invention is shown in FIG. 8 and is similar to that of the third embodiment, and so like features retain the same reference numerals and a detailed description thereof will not be repeated.

A difference between the needle assembly 416 of the fifth embodiment and that of the third embodiment is that the spacer element 31 is integrally formed with the needle holder 27. The spacer element 31 is made of a rigid material, and, contrary to the one in the needle assemblies described above, is therefore not deformable. The spacer element 31 covers the distal end 19 of the needle 17. The sealing membrane 32 is sealed onto the spacer element 31 and ensures the protection of the distal end 19. The proximal end 18 is protected by a rigid needle shield 26. However, the proximal end 18 could be protected by a compressible tube as described in the fourth embodiment above.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device or medicament delivery device assembly may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), an implantable device (e.g., drug- or API-coated stent, capsule), or a feeding system for the gastrointestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®);

B29-N—(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten. An example of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in certain aspects of the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. An injection needle assembly for coupling to a medicament delivery device which comprises a cartridge for medicament, the injection needle assembly comprising:
   an injection needle holder;
   an injection needle fixed to the injection needle holder, the injection needle having a proximal end and a distal end; and
   a sealing assembly for sealing the distal end of the injection needle, wherein the sealing assembly comprises (i) a spacer element surrounding the distal end of the injection needle, wherein the spacer element is deformable and (ii) a separate sealing membrane configured to seal the distal end of the injection needle prior to the injection needle assembly being coupled to the medicament delivery device.

2. The injection needle assembly according to claim 1, wherein:
   the sealing assembly is movable between a storage configuration and a use configuration;
   in the storage configuration, the spacer element is in an extended state such that the spacer element entirely surrounds the distal end of the injection needle; and
   in the use configuration, the spacer element is in a retracted state such that the distal end of the injection needle extends beyond the spacer element.

3. The injection needle assembly according to claim 2, wherein in the storage configuration, the spacer element is located within the sealing membrane such that the sealing membrane seals the spacer element.

4. The injection needle assembly according to claim 2, wherein the distal end of the injection needle is configured to pierce the sealing membrane when the sealing assembly moves from the storage configuration towards the use configuration.

5. The injection needle assembly according to claim 1, wherein the spacer element comprises a central passage through which the injection needle extends.

6. The injection needle assembly according to claim 5, wherein the central passage is configured such that the injection needle is not in contact with the spacer element.

7. The injection needle assembly according to claim 1, wherein the spacer element is made of a resilient material.

8. The injection needle assembly according to claim 1, wherein a part of the spacer element is fixed to the injection needle holder.

9. The injection needle assembly according to claim 1, comprising a deformable injection needle shield for shielding the proximal end of the injection needle.

10. The injection needle assembly according to claim 9, wherein:
    the injection needle shield is deformable between a shielding position and a retracted position;
    in the shielding position, the injection needle shield is in an extended state such that the injection needle shield entirely surrounds the proximal end of the injection needle; and
    in the retracted position, the injection needle shield is in a retracted state such that the proximal end of the injection needle extends beyond the injection needle shield.

11. The injection needle assembly according to claim 1, wherein the injection needle holder comprises an engaging element configured to engage a corresponding engaging element of the medicament delivery device to connect the injection needle assembly to the medicament delivery device.

12. The injection needle assembly according to claim 1, wherein the sealing membrane comprises a deformable cover.

13. A medicament delivery device assembly comprising:
    an injection needle assembly for coupling to a medicament delivery device which comprises a cartridge for medicament, the injection needle assembly comprising:
        an injection needle holder;
        an injection needle fixed to the injection needle holder, the injection needle having a proximal end and a distal end; and
        a sealing assembly for sealing the distal end of the injection needle, wherein the sealing assembly comprises (i) a spacer element surrounding the distal end of the injection needle, wherein the spacer element is deformable, and (ii) a separate sealing membrane configured to seal the distal end of the injection needle prior to the injection needle assembly being coupled to the medicament delivery device; and
    the medicament delivery device.

14. The medicament delivery device assembly according to claim 13, wherein the injection needle assembly is releasably connected to the medicament delivery device.

15. The medicament delivery device assembly according to claim 13, wherein the cartridge contains medicament.

16. The medicament delivery device assembly according to claim 13, wherein:
    the sealing assembly is movable between a storage configuration and a use configuration,
    in the storage configuration, the spacer element is in an extended state such that the spacer element entirely surrounds the distal end of the injection needle, and
    in the use configuration, the spacer element is in a retracted state such that the distal end of the injection needle extends beyond the spacer element.

17. A method of assembling a medicament delivery device assembly, the method comprising:
    providing a medicament delivery device;
    providing an injection needle assembly for coupling to the medicament delivery device which comprises a cartridge for medicament, the injection needle assembly comprising an injection needle holder, an injection needle fixed to said injection needle holder and having a proximal end and a distal end, and a sealing assembly having (i) a spacer element surrounding the distal end of the injection needle, wherein the spacer is deformable, and (ii) a separate sealing membrane configured to seal the distal end of the injection needle prior to the injection needle assembly being coupled to the medicament delivery device; and
    coupling the injection needle assembly to the medicament delivery device.

* * * * *